US010729370B2

(12) United States Patent
Lin et al.

(10) Patent No.: US 10,729,370 B2
(45) Date of Patent: Aug. 4, 2020

(54) MOBILE SENSOR SYSTEM AND METHODS FOR USE

(71) Applicant: Rosalind Franklin University of Medicine and Science, North Chicago, IL (US)

(72) Inventors: Fang Lin, North Chicago, IL (US); Sai V. Yalla, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 1086 days.

(21) Appl. No.: 14/964,690

(22) Filed: Dec. 10, 2015

(65) Prior Publication Data

US 2016/0166193 A1      Jun. 16, 2016

Related U.S. Application Data

(60) Provisional application No. 62/090,171, filed on Dec. 10, 2014.

(51) Int. Cl.
```
A61B 5/00      (2006.01)
A61B 3/113     (2006.01)
A61B 5/11      (2006.01)
```
(52) U.S. Cl.
CPC ............ *A61B 5/4064* (2013.01); *A61B 3/113* (2013.01); *A61B 5/0051* (2013.01); *A61B 5/11* (2013.01);
(Continued)

(58) Field of Classification Search
CPC ....... A61B 5/6803; A61B 5/11; A61B 5/4023; A61B 3/113
(Continued)

(56) References Cited

U.S. PATENT DOCUMENTS 4,797,736 A * 1/1989 Kloots .................. F21V 21/084
                                              348/370
8,979,665 B1* 3/2015 Najafi ................. G09B 19/0038
                                              473/269
(Continued)

OTHER PUBLICATIONS

Defense and Veterans Brain Injury Center. DoD Worldwide TBI Numbers. (2014). at <http://dvbic.dcoe.mil/dod-worldwide-numbers-tbi>.

(Continued)

*Primary Examiner* — John R Downey
(74) *Attorney, Agent, or Firm* — McDonnell Boehnen Hulbert & Berghoff LLP

(57) ABSTRACT

The present disclosure provides a system including one or more sensors, a mounting system configured to removeably mount a computing device such that a camera of the computing device is positioned facing an eye of a subject, and a control system. The control system is configured to (a) receive sensor data from the one or more sensors, (b) determine whether the sensor data is indicative of balance instability of the subject, (c) track a position of the eye of the subject to assess vestibular dysfunction, (d) determine whether the camera data is indicative of vestibular dysfunction of the subject, and (e) in response to (i) the sensor data being indicative of balance instability of the subject and/or (ii) the camera data being indicative of vestibular dysfunction of the subject, display an indication of symptoms that are characteristic of a traumatic brain injury or concussion.

18 Claims, 9 Drawing Sheets

(52) U.S. Cl.
CPC .......... *A61B 5/4023* (2013.01); *A61B 5/4863* (2013.01); *A61B 5/6831* (2013.01); *A61B 2562/0219* (2013.01); *A61B 2562/0223* (2013.01)

(58) Field of Classification Search
USPC ........................................ 600/301, 558, 595
See application file for complete search history.

(56) References Cited

U.S. PATENT DOCUMENTS

| | | | | |
|---|---|---|---|---|
| 2008/0023002 | A1* | 1/2008 | Guelzow | A42B 3/042 128/201.24 |
| 2008/0278685 | A1* | 11/2008 | MacDougall | A61B 3/113 351/206 |
| 2009/0018419 | A1* | 1/2009 | Torch | A61B 3/112 600/318 |
| 2013/0274587 | A1* | 10/2013 | Coza | A61B 5/6804 600/409 |
| 2014/0024971 | A1* | 1/2014 | Bunn | A61B 5/11 600/595 |
| 2016/0007849 | A1* | 1/2016 | Krueger | A61B 3/113 600/301 |
| 2016/0007921 | A1* | 1/2016 | Galea | G02B 27/0093 600/301 |
| 2016/0213301 | A1* | 7/2016 | Port | A61B 3/113 |

OTHER PUBLICATIONS

U.S. Department of Defense. Report on the Impact of Deployment of Members of the Armed Forces on Their Dependent Children Oct. 2010. 1-81 (2010). at <http://www.militaryhomefront.dod.mi1/12038/ProjectDocuments/MilitaryHOMEFRONT/Reports/Report_to_Congress_on_Impact_of_Deployment_on_Military_Children.pdf>.
Hoge, C. W. et al. Mild Traumatic Brain Injury in U.S. Soldiers Returning from Iraq. N. Engl. J. Med. 358, 453-463 (2008).
Terrio, H. et al. Traumatic brain injury screening: preliminary findings in a US Army Brigade Combat Team. J. Head Trauma Rehabil. 24, 14-23 (2009).
Lei-Rivera, L., Sutera, J., Galatioto, J. a, Hujsak, B. D. & Gurley, J. M. Special tools for the assessment of balance and dizziness in individuals with mild traumatic brain injury. NeuroRehabilitation 32, 463-72 (2013).
Chandrasekhar S., S. The assessment of balance and dizziness in the TBI patient. NeuroRehabilitation 32, 445-454 (2013).
Akin, F. W. & Murnane, O. D. Head injury and blast exposure: vestibular consequences. Otolaryngol. Clin. North Am. 44, 323-34, viii (2011).
Black, K et al. Sitting balance following brain injury : does it predict outcome ? 14, (2000).
Shumway-Cook, A; Olmscheid, R. A systems analysis of postural dyscontrol in traumatically braininjured patients. J Head Trauma Rehabil. 5, 51-62 (1990).
VA. VA TBI Instruments User Manual Increment 6 Version 5. 109 (2014). at <http://www.va.gov/vdl/documents/Clinical/Traumatic_Brain_injury/tbiinsum_doc>.
King, L. A. et al. Instrumenting the balance error scoring system for use with patients reporting persistent balance problems after mild traumatic brain injury. Arch. Phys. Med. Rehabil. 95, 353-9 (2014).
DCoE. Assessment and Management of Dizziness Associated with Mild TBI Introduction and Background. DCoE Clin. Recomm. (2012). at <http://dvbic.dcoe.mil/sites/default/files/Dizziness_Associated_with_Mild_TBI_Clinical_Recommendation.pdf>.
Cifu, D. et al. Clinical practice guideline: Management of Concussion/Mild Traumatic Brain Injury. J. Rehabil. Res. Dev. 46, CP1 (2009).
Iverson, G. L., Kaarto, M. L. & Koehle, M. S. Normative data for the balance error scoring system: implications for brain injury evaluations. Brain Inj. 22, 147-52 (2008).

Cripps, A & Livingston C., S. The Value of Balance-Assessment Measurements in Identifying and Monitoring Acute Postural Instability Among Concussed Athletes. J. Sport Rehabil. 22, 67-71 (2013).
Riemann, B. L. & Guskiewicz, K. M. Effects of Mild Head Injury on Postural Stability as Measured Through Clinical Balance Testing. J. Athl. Train. (National Athl. Trainers' Assoc. 35, 19 (2000).
Defense and Veteran Brain Injury Center. Combat Medic/Corpsman Algorithm (Pre-hospital/no medical officer in the immediate area). Concussion Manag. Deployed Settings (2012). at <http://www.dcoe.mil/content/Navigation/Documents/DCoE_Concussion_Management_Algorithm_Cards.pdf>.
Barth, J. T., Isler, W. C., Helmick, K. M., Wingler, L. M. & Jaffee, M. S. Acute battlefield assessment of concussion/mild TBI and return-to-duty evaluations. Defense and Veterans Brain Injury Center 127-174 (2010). at <http://ovidsp.ovid.com/ovidweb.cgi?T=JS&CSC=Y&NEWS=N&PAGE=fulltext&D=psyc6&AN=2010-05661-006\nhttp://sfx.kb.dk.ep.jernadgang.kb.dk/sfx_local?sid=OVID:psycdb&id=pmid:&id=doi:&issn=&isbn=9780826104489&volume=&issue=&spage=127&pages=127-174&date=2010&title=>.
Lin, F., Perlmutter, S., Lee, A. & Makhsous, M. Quantification of seated trunk motion in post-stroke individuals. in Society for Neuroscience (2009).
Perlmutter, S., Lin, F. & Makhsous, M. Quantitative analysis of static sitting posture in chronic stroke. Gait Posture 32, 53-6 (2010).
Perlmutter, S., Makhsous, M. & Lin, F. Impairment in sitting postural trunk control post stroke. in International Stroke Conference (2009).
Kelly, C. et al. Fear of Falling Is Prevalent in Older Adults with Diabetes Mellitus But Is Unrelated to Level of Neuropathy. J Am Pod. Med Assoc 103, 480-8 (2013).
Grewal S, G. et al. Balance rehabilitation: promoting the role of virtual reality in patients with diabetic peripheral neuropathy. J. Am. Podiatr. Med. Assoc. 103, 498-507 (2013).
Grewal, G. et al. Virtualizing the assessment: A novel pragmatic paradigm to evaluate lower extremity joint perception in diabetes. Gerontology 58, 463-471 (2012).
Lin, F., Ermoloff, J., Moore, J., Painter, B. & Pittenger, K. Balance after Total Hip Arthroplasty (THA) and the Effect of Hip Abductor Strength. in The 2014 International Society for Posture & Gait Research World Congress (2014).
Putnam, C. et al. Supporting Therapists in Motion-Based Gaming for Brain Injury Rehabilitation. in DePaul-RFUMS Research Retreat 2014 (2014).
Yalla V., S. et al. An immediate effect of custom-made ankle foot orthoses on postural stability in older adults. Clin. Biomech. 29, 1081-1088 (2014).
Najafi, B., Aminian, K., Loew, F., Blanc, Y. & Robert, P. a. Measurement of stand-sit and sit-stand transitions using a miniature gyroscope and its application in fall risk evaluation in the elderly. IEEE Trans. Biomed. Eng. 49, 843-51 (2002).
Najafi, B, Helbostad, J. L., Moe-Nilssen, R., Zijlstra, W. & Aminian, K. Does walking strategy in older people change as a function of walking distance? Gait Posture 29, 261-6 (2009).
Najafi, B. et al. Assessing postural control and postural control strategy in diabetes patients using innovative and wearable technology. J. Diabetes Sci. Technol. 4, 780-91 (2010).
Asawavichiangianda, S., Fujimoto, M., Mai, M., Desroches, H. & Rutka, J. Significance of Head-shaking Nystagmus in the Evaluation of the Dizzy Patient. Acta Oto-Laryngologica 119, 27-33 (1999).
Jacobson, G., Newman, C. & Safadi, I. Sensitivity and specificity of the head-shaking test for detecting vestibular system abnormalities. Ann Otol Rhinol Laryngol 99, 539-42 (1990).
Schubert, M. C., Tusa, R. J., Grine, L. E. & Herdman, S. J. Optimizing the Sensitivity of the Head Thrust Test for Identifying Vestibular Hypofunction. Phys. Ther. 84 , 151-158 (2004).
Nuti, D. & Mandalá, M. Sensitivity and specificity of mastoid vibration test in detection of effects of vestibular neuritis. Acta Otorhinolaryngol. Ital. 25, 271-276 (2005).

(56) References Cited

OTHER PUBLICATIONS

DCoE. Assessment and management of dizziness associated with mild TBI. (2012). at <http://www.dcoe.mil/content/Navigation/Documents/Dizziness_Associated_with_Mild_TBI_Clinical_Recommendation.pdf>.

Perlmutter, S., Lin, F. & Dewald, J. P. A. Development of a Device for Measurement of Multi-Directional Isometric Trunk Kinetics in a Seated Position. IEEE Trans. Neural Syst. Rehabil. Eng. 22, 344-351 (2014).

Moon, H., Chellappa, R. & Rosenfeld, A. Optimal edge-based shape detection. IEEE Trans. Image Process. A Publ. IEEE Signal Process. Soc. 11, 1209-1226 (2002).

Boulos, M. N. K, Wheeler, S., Tavares, C. & Jones, R. How smartphones are changing the face of mobile and participatory healthcare: an overview, with example from eCAALYX. Biomed. Eng. Online 10, 24 (2011).

Goadrich, M. H. & Rogers, M. P. Smart smartphone development. Proc. 42nd ACM Tech. Symp. Comput. Sci. Educ. 607 (2011). at <http://ezproxy.rosalindfranklin.edu:2048/login?url=http://search.ebscohost.com/login.aspx?direct=true&db=edb&AN=83604085&site=eds-live&scope=site>.

McDaniel, P. Bloatware Comes to the Smartphone. IEEE Secur. Priv. Mag. 10, 85 (2012).

Iijima, A., Minamitani, H. & Ishikawa, N. Image analysis of quick phase eye movements in nystagmus with high-speed video system. Med. Biol. Eng. Comput. 39, 2-7 (2001).

Karlberg, M. et al. Vibration-induced ocular torsion and nystagmus after unilateral vestibular deafferentation. Brain 126, 956-964 (2003).

Patel, M., Fransson, P. A., Lush, D. & Gomez, S. The effect of foam surface properties on postural stability assessment while standing. Gait Posture 28, 649-56 (2008).

Virzi, R. A. Refining the test phase of usability evaluation: How many subjects is enough? Hum. Factors 34, 457-468 (1992).

Vanvoorhis, C. R. W. & Morgan, B. L Understanding Power and Rules of Thumb for Determining Sample Sizes. Tutorials Quant. Methods 3, 43-50 (2007).

Bryk, A. S. & Raudenbush, S. W. Heterogeneity of variance in experimental studies: A challenge to conventional interpretations. Psychol. Bull. 104, 396-404 (1988).

Green, S. B. How Many Subjects Does It Take to Do a Regression Analysis? Multivariate Behav. Res. 26, 499-510 (1991).

Faul, F., Erdfelder, E., Buchner, A. & Lang, A.-G. Statistical power analyses using G*Power 3.1: tests for correlation and regression analyses. Behay. Res. Methods 41, 1149-1160 (2009).

Defense and Veterans Brain Injury Center. DoD Worldwide TBI Numbers [Internet]. 2014. Available from: http://dvbic.dcoe.mil/sites/default/files/uploads/Worldwide Totals 2000-2014Q2-Sept19th.pdf.

Lei-Rivera L, Sutera J, Galatioto J a, Hujsak BD, Gurley JM. Special tools for the assessment of balance and dizziness in individuals with mild traumatic brain injury. NeuroRehabilitation [Internet]. Jan. 2013 [cited Dec. 9, 2014];32(3):463-72. Available from: http://www.ncbi.nlm.nih.gov/pubmed/23648601.

DCoE. Assessment and management of dizziness associated with mild TBI [Internet]. 2012. Available from: http://www.dcoe.mil/content/Navigation/Documents/Dizziness_Associated_with_Mild_TBI_Clinical_Recommendation.pdf.

Chandrasekhar S. S. The assessment of balance and dizziness in the TBI patient. NeuroRehabilitation; May 2013;32 (3):445-54. Available from: http://ezproxy.rosalindfranklin.edu:2048/login?url=http://search.ebscohost.com/login.aspx?direct=true&db=ccm&AN=2012099931&site=eds-live&scope=site.

Shimmer. Shimmer3 Development Kit [Internet]. [cited Dec. 8, 2014]. Available from: http://www.shimmersensing.com/shop/shimmer3-development-kit.

Kelly C, Fleischer A, Yalla S, Grewal G, Albright R, Berns D, et al. Fear of Falling Is Prevalent in Older Adults with Diabetes Mellitus But Is Unrelated to Level of Neuropathy. J Am Pod Med Assoc. 2013;103(6):480-8.

Najafi B, Aminian K, Loew F, Blanc Y, Robert P a Measurement of stand-sit and sit-stand transitions using a miniature gyroscope and its application in fall risk evaluation in the elderly. IEEE Trans Biomed Eng [Internet]. Aug. 2002;49(8):843-51. Available from: http://www.ncbi.nlm.nih.gov/pubmed/12148823.

Najafi B, Horn D, Marclay S, Crews RT, Wu S, Wrobel JS. Assessing postural control and postural control strategy in diabetes patients using innovative and wearable technology. J Diabetes Sci Technol [Internet]. Jul. 2010;4(4):780-91. Available from: http://www.pubmedcentral.nih.gov/articlerender.fcgi?artid=2909506&tool=pmcentrez&rendertype=abstract.

MacDougall HG, Weber KP, McGarvie LA, Halmagyi GM, Curthoys IS. The video head impulse test: Diagnostic accuracy in peripheral vestibulopathy. Neurology [Internet]. Halmagyi, G. M., Royal Prince Alfred Hospital, Camperdown, Sydney, NSW, Australia, 2050: Lippincott Williams & Wilkins; Oct. 6, 2009;73(14):1134-44. Available from: http://ezproxy.rosalindfranklin.edu:2048/login?url=http://search.ebscohost.com/login.aspx?direct=true&db=psyh&AN=2009-18729-009&site=eds-live&scope=site.

Black K, Zafonte R, Illis Scottm, Cy Nan, Nt Desa, Wood D, et al. Sitting balance following brain injury : does it predict outcome ? 2000;14(2):141-52.

* cited by examiner

US 10,729,370 B2

MOBILE SENSOR SYSTEM AND METHODS FOR USE

CROSS-REFERENCE TO RELATED APPLICATIONS

This application claims the benefit of the filing date of U.S. Provisional Patent Application Ser. No. 62/090,171, filed Dec. 10, 2014, which is hereby incorporated by reference in its entirety.

BACKGROUND

Unless otherwise indicated herein, the materials described in this section are not prior art to the claims in this application and are not admitted to be prior art by inclusion in this section.

Traumatic brain injury (TBI) occurs when an external force traumatically injures the brain. TBI is common in soldiers in military training and combat, as well as athletes participating in sporting events, among other activities. TBI related symptoms can be somatic such as headache, dizziness, sleep disturbance, balance problems, nausea, fatigue, and cognitive deficits. Balance and orientation are maintained through the coordination of vestibular function, vision, and proprioception among which the vestibular system plays a critical role because its dysfunction will override the inputs from the other two systems. A TBI, especially a blast injury to the head can result in dysfunction in peripheral and/or central vestibular system that affect a person's ability to maintain postural balance.

A fast and accurate assessment of the balance and vestibular function of individuals that have sustained TBI can help reach a more accurate diagnosis sooner and aid in efficient and accurate triaging. There are many existing clinical tools and bedside tests that have been proven useful in assessment in individuals with TBI. However, administering such tests usually requires specific training and experience that an individual on-site may not possess. Moreover, many of these existing tests involve subjective evaluation of the examiner and provide qualitative measures that may complicate analysis and could yield poor inter-rater consistency. Although the more severe forms of TBI are often identified and triaged immediately, mild TBI (mTBI), which is also known as a concussion, can be easily missed or overlooked given there are frequently no obvious signs of injury. The absence of an early and accurate diagnosis places service members and sports players at risk for recurrent head trauma and delayed treatment, which could potentially lead to more significant injuries. Therefore, there is a need for a system that is capable of quickly obtaining on-site objective and quantitative data for balance and vestibular function for individuals with TBI may be desirable.

SUMMARY

An example portable mobile system and methods for detecting symptoms that are characteristic of TBI or a concussion are disclosed. Such a system may include a computing device, one or more sensors, and a mounting system to support the computing device at a specific distance to target an eye of the subject. A camera on the computing device may be utilized to quantify eye movement to detect the presence of vestibular dysfunction, such as nystagmus. In addition, the one or more sensors may provide objective measures of postural sway during sitting and standing to quantify postural balance of the subject. The combination of assessment of both balance and vestibular function may be used to quickly and objectively evaluate the potential related symptoms in individuals who may have sustained TBI.

Thus, in one embodiment, a system is provided. The system may include one or more sensors. The system may further include a mounting system configured to removeably mount a computing device such that a camera of the computing device is positioned facing an eye of a subject. The system may further include a control system, wherein the control system is configured to (a) receive sensor data from the one or more sensors, wherein the one or more sensors are configured to be removeably positioned on the subject, (b) determine whether the sensor data is indicative of balance instability of the subject, (c) track a position of the eye of the subject for a given time period to assess vestibular dysfunction based on data received from the camera of the computing device, (d) determine whether the camera data is indicative of vestibular dysfunction of the subject, (e) in response to (i) the sensor data being indicative of balance instability of the subject and/or (ii) the camera data being indicative of vestibular dysfunction of the subject, cause the computing device to provide for display an indication that the subject has symptoms that are characteristic of a traumatic brain injury or concussion, and (f) in response to both (i) the sensor data not being indicative of balance instability of the subject and (ii) the camera data not being indicative of vestibular dysfunction of the subject, cause the computing device to provide for display an indication that the subject does not have symptoms that are characteristic of a traumatic brain injury or concussion.

In another embodiment, a method is provided. The method may include (a) positioning one or more sensors on a subject, (b) receiving, at a computing device, sensor data from one or more sensors positioned on the subject, (c) determining, by the computing device, whether the sensor data is indicative of balance instability of the subject, (d) removeably coupling the computing device to a mounting system such that a camera of the computing device is positioned facing an eye of the subject, (e) tracking, by the computing device, a position of the eye of the subject for a given time period to assess vestibular dysfunction based on data received from the camera of the computing device, (f) determining, by the computing device, whether the camera data is indicative of vestibular dysfunction of the subject, (g) in response to (i) the sensor data being indicative of balance instability of the subject and/or (ii) the camera data being indicative of vestibular dysfunction of the subject, causing the computing device to provide for display an indication that the subject has symptoms that are characteristic of a traumatic brain injury or concussion, and (h) in response to both (i) the sensor data not being indicative of balance instability of the subject and (ii) the camera data not being indicative of vestibular dysfunction of the subject, causing the computing device to provide for display an indication that the subject does not have symptoms that are characteristic of a traumatic brain injury or concussion.

In another embodiment, a non-transitory computer-readable storage medium is provided storing instructions that, when executed by one or more processors of a computing device, cause the computing device to perform functions. The functions may include receiving sensor data from one or more sensors positioned on a subject. The functions may further include determining whether the sensor data is indicative of balance instability of the subject. The functions may further include, in response to the sensor data being indicative of balance instability of the subject, causing the computing device to provide for display an indication that the subject has symptoms that are characteristic of a traumatic brain injury or concussion. The functions may further include, in response the sensor data not being indicative of balance instability of the subject, causing the computing device to provide for display an indication that the subject does not have symptoms of balance instability that are characteristic of a traumatic brain injury or concussion.

In another embodiment, a non-transitory computer-readable storage medium is provided storing instructions that, when executed by one or more processors of a computing device, cause the computing device to perform functions. The functions may include tracking a position of an eye of the subject for a given time period to assess vestibular dysfunction based on data received from a camera of the computing device, wherein the computing device is removeably coupled to a mounting system such that the camera of the computing device is positioned facing the eye of the subject. The functions may further include determining the camera data is indicative of vestibular dysfunction of the subject. The functions may further include, in response to the camera data being indicative of vestibular dysfunction of the subject, causing the computing device to provide for display an indication that the subject has symptoms that are characteristic of a traumatic brain injury or concussion. The functions may further include, in response to the camera data not being indicative of vestibular dysfunction of the subject, causing the computing device to provide for display an indication that the subject does not have abnormal eye movement symptoms that are characteristic of a traumatic brain injury or concussion.

In yet another embodiment, a non-transitory computer-readable storage medium is provided storing instructions that, when executed by one or more processors of a computing device, cause the computing device to perform functions. The functions may include receiving sensor data from one or more sensors positioned on a subject. The functions may further include determining whether the sensor data is indicative of balance instability of the subject. The functions may further include tracking a position of an eye of the subject for a given time period to assess vestibular dysfunction based on data received from a camera of the computing device, wherein the computing device is removeably coupled to a mounting system such that the camera of the computing device is positioned facing the eye of the subject. The functions may further include determining whether the camera data is indicative of vestibular dysfunction of the subject. The functions may further include, in response to (i) the sensor data being indicative of balance instability of the subject and/or (ii) the camera data being indicative of vestibular dysfunction of the subject, causing the computing device to provide for display an indication that the subject has symptoms that are characteristic of a traumatic brain injury or concussion. The functions may further include, in response to both (i) the sensor data not being indicative of balance instability of the subject and (ii) the camera data not being indicative of vestibular dysfunction of the subject, causing the computing device to provide for display an indication that the subject does not have symptoms that are characteristic of a traumatic brain injury or concussion.

These as well as other aspects, advantages, and alternatives, will become apparent to those of ordinary skill in the art by reading the following detailed description, with reference where appropriate to the accompanying drawings.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

The present disclosure provides systems and methods for detecting symptoms that are characteristic of a traumatic brain injury or concussion. As discussed above, there is a need for a portable system to provide quick on-site assessment for both balance and vestibular function in initial TBI screening. By quickly obtaining on-site objective and quantitative data for balance and vestibular function for patients who may have TBI, efficient and accurate triaging of such patients may thereby occur. If it is determined using the systems and methods described herein that a subject has symptoms that are characteristic of a traumatic brain injury or concussion, that subject may be sent to a hospital or other medical establishment for further testing and assessment.

Figure 1:
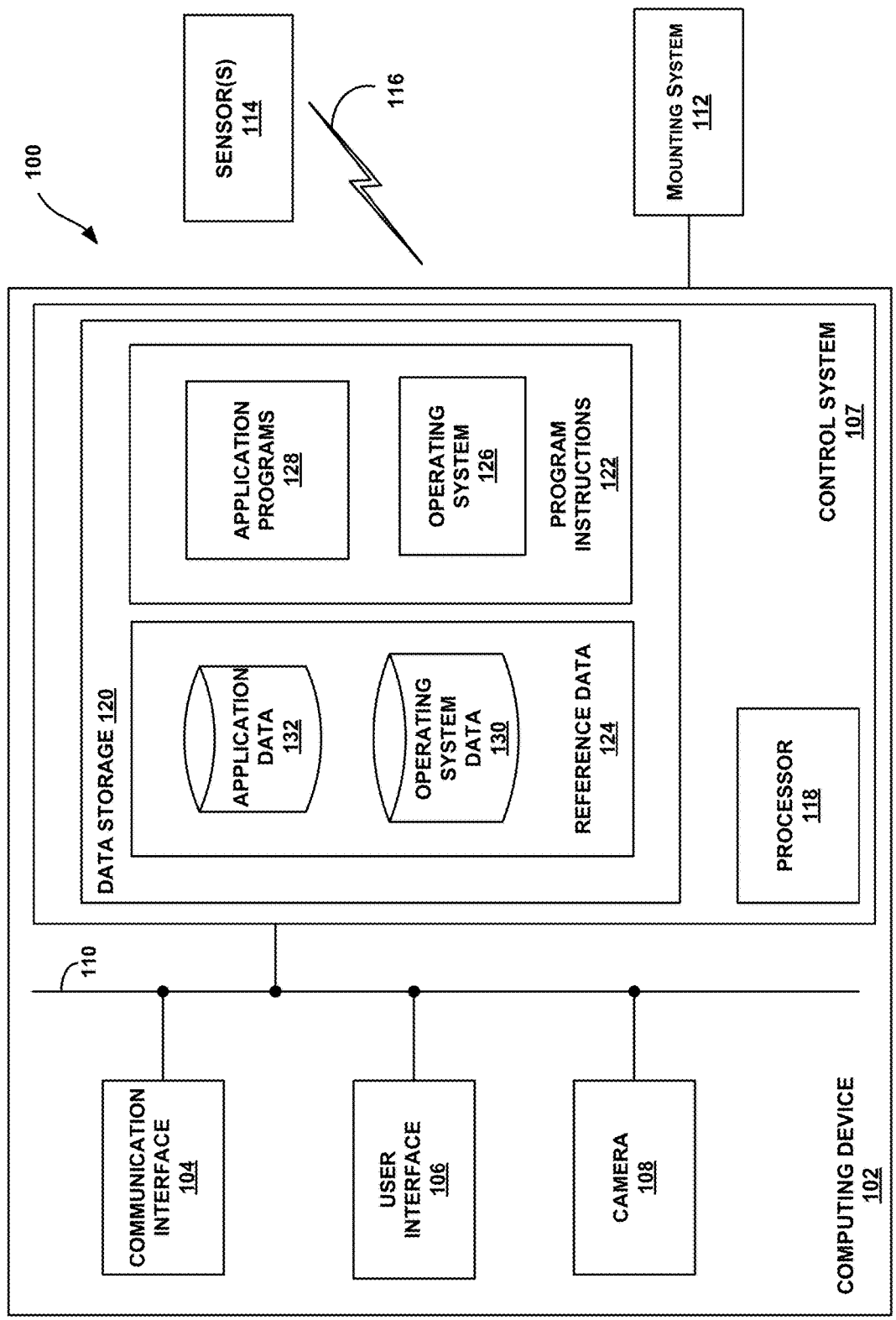
FIG. 1 is a simplified block diagram illustrating an example system, according to an example embodiment.

With reference to the Figures, FIG. 1 illustrates a simplified block diagram of an example system 100 for detecting symptoms that are characteristic of a traumatic brain injury or concussion. As shown in FIG. 1, the system 100 may include a computing device 102 comprising a communication interface 104, a user interface 106, a control system 107, and a camera 108, all of which may be communicatively linked together by a system bus, network, or other connection mechanism 110. The system 100 may further include a mounting system 112 configured to removeably mount the computing device 102 such that the camera 108 of the computing device 102 is positioned facing an eye of a subject. The system 100 may further include one or more sensors 114. The computing device 102 may be configured to communicate with the one or more sensors 114 using a communication link 116, such as a wired or wireless connection.

By way of example and without limitation, computing device 102 may be a cellular mobile telephone (e.g., a smartphone), a still camera, a video camera, a computer (such as a desktop, notebook, tablet, or handheld computer), a personal digital assistant (PDA), a wearable computing device, or some other type of device equipped with at least some image capture and/or image processing capabilities.

Communication interface 104 may function to allow computing device 102 to communicate, using analog or digital modulation, with other devices, access networks, and/or transport networks. Thus, communication interface 104 may facilitate circuit-switched and/or packet-switched communication, such as plain old telephone service (POTS) communication and/or Internet protocol (IP) or other packetized communication. For instance, communication interface 104 may include a chipset and antenna arranged for wireless communication with a radio access network or an access point. Also, communication interface 104 may take the form of or include a wireline interface, such as an Ethernet, Universal Serial Bus (USB), or High-Definition Multimedia Interface (HDMI) port. Communication interface 104 may also take the form of or include a wireless interface, such as a Wifi, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 104. Furthermore, communication interface 104 may comprise multiple physical communication interfaces (e.g., a Wifi interface, a short range wireless interface, and a wide-area wireless interface).

User interface 106 may function to allow computing device 102 to interact with a human or non-human user, such as to receive input from a user and to provide output to the user. Thus, user interface 106 may include input components such as a keypad, keyboard, touch-sensitive or presence-sensitive panel, computer mouse, trackball, joystick, microphone, and so on. User interface 106 may also include one or more output components such as a display screen which, for example, may be combined with a presence-sensitive panel. The display screen may be based on CRT, LCD, and/or LED technologies, or other technologies now known or later developed. User interface 106 may also be configured to generate audible output(s), via a speaker, speaker jack, audio output port, audio output device, earphones, and/or other similar devices.

Control system 107 may include a processor 118 and data storage 120. Processor 118 may comprise one or more general purpose processors—e.g., microprocessors—and/or one or more special purpose processors—e.g., digital signal processors (DSPs), graphics processing units (GPUs), floating point units (FPUs), network processors, or application-specific integrated circuits (ASICs). In some instances, special purpose processors may be capable of image processing, image alignment, and merging images, among other possibilities. Data storage 120 may include one or more volatile and/or non-volatile storage components, such as magnetic, optical, flash, or organic storage, and may be integrated in whole or in part with processor 118. Data storage 120 may include removable and/or non-removable components.

Processor 118 may be capable of executing program instructions 122 (e.g., compiled or non-compiled program logic and/or machine code) stored in data storage 120 to carry out the various functions described herein. Therefore, data storage 120 may include a non-transitory computer-readable medium, having stored thereon program instructions that, upon execution by computing device 102, cause computing device 102 to carry out any of the methods, processes, or functions disclosed in this specification and/or the accompanying drawings. The execution of program instructions 122 by processor 118 may result in processor 118 using reference data 124.

By way of example, program instructions 122 may include an operating system 126 (e.g., an operating system kernel, device driver(s), and/or other modules) and one or more application programs 128 installed on computing device 102. Similarly, reference data 124 may include operating system data 130 and application data 132. Operating system data 130 may be accessible primarily to operating system 126, and application data 132 may be accessible primarily to one or more of application programs 128. Application data 132 may be arranged in a file system that is visible to or hidden from a user of computing device 102.

Application programs 128 may communicate with operating system 130 through one or more application programming interfaces (APIs). These APIs may facilitate, for instance, application programs 128 reading and/or writing application data 132, transmitting or receiving information via communication interface 104, receiving and/or displaying information on user interface 106, and so on.

In some examples, application programs 128 may be referred to as "apps" for short. Additionally, application programs 128 may be downloadable to computing device 102 through one or more online application stores or application markets. However, application programs can also be installed on computing device 102 in other ways, such as via a web browser or through a physical interface (e.g., a USB port) on computing device 102.

Camera 108 may include an image sensor and associated optical elements such as lenses. Camera 108 may offer zoom capabilities or could have a fixed focal length. In other embodiments, interchangeable lenses could be used with camera 108. Camera 108 may have a variable mechanical aperture and a mechanical and/or electronic shutter. Camera 108 also could be configured to capture still images, video images, or both. Further, camera 108 could represent a monoscopic, stereoscopic, or multiscopic camera. Camera 108 may include or be associated with an illumination component that provides a light field to illuminate a target object. For instance, an illumination component could provide flash or constant illumination of the target object. An illumination component could also be configured to provide a light field that includes one or more of structured light, polarized light, and light with specific spectral content. Other types of light fields known and used to recover three-dimensional (3D) models from an object are possible within the context of the embodiments herein.

Camera 108 may further include or be associated with an ambient light sensor that may continuously or from time to time determine the ambient brightness of a scene that the camera can capture. In some devices, the ambient light sensor can be used to adjust the display brightness of a screen associated with the camera (e.g., a viewfinder). When the determined ambient brightness is high, the brightness level of the screen may be increased to make the screen easier to view. When the determined ambient brightness is low, the brightness level of the screen may be decreased, also to make the screen easier to view as well as to potentially save power.

An image capture by the camera 108 could be triggered by activating a shutter button, pressing a softkey on user interface 106, or by some other mechanism. Depending upon the implementation, the images could be captured automatically at a specific time interval, for example, upon pressing shutter button, upon appropriate lighting conditions of the target object, upon moving the camera 108 a predetermined distance, or according to a predetermined capture schedule. As such, camera 108 may be controlled at least in part by software executed by processor 118.

Figure 2:
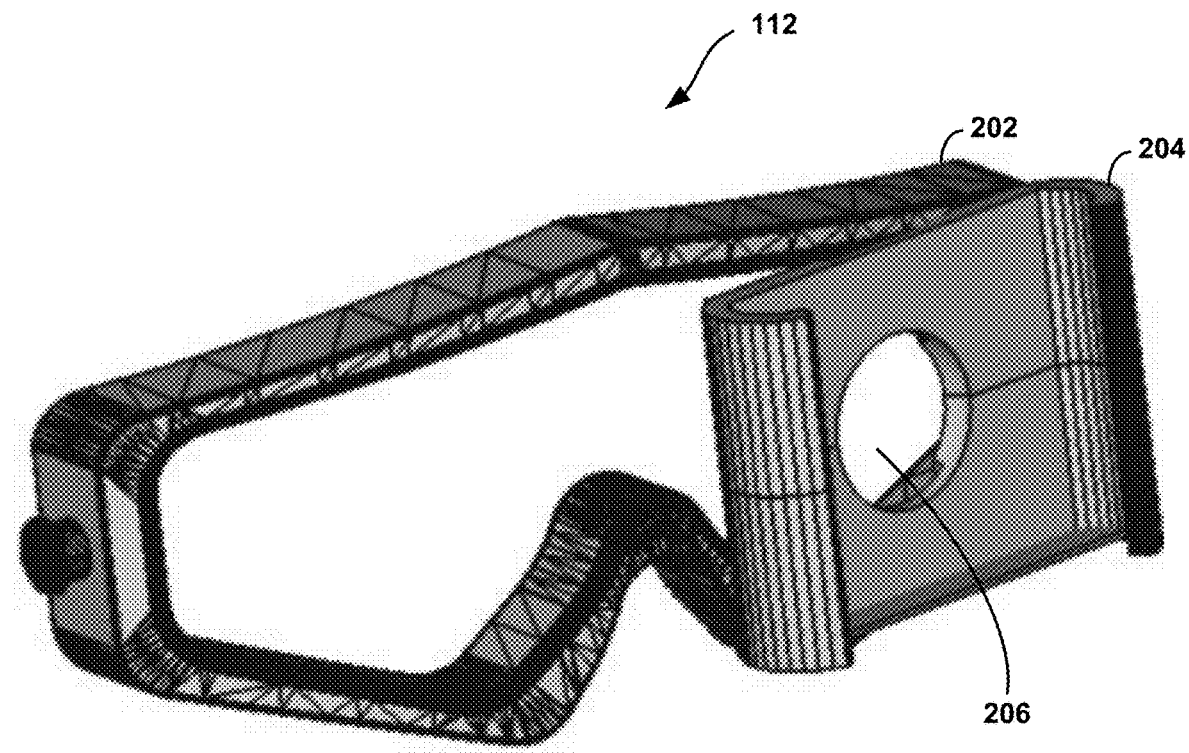
FIG. 2 illustrates an example mounting system, according to an example embodiment.

Mounting system 112 may be configured to removeably mount computing device 102 such that camera 108 is positioned facing an eye of a subject. In one example, mounting system 112 is implemented as part of or takes the form of a head-mountable device. In one particular example, as shown in FIG. 2, the mounting system 112 may include goggles 202 with a mounting clip 204 coupled to the goggles 202. The goggles 202 may further include a strap (not shown) configured to hold the goggles 202 to the face of the subject. The mounting clip 204 may include two curved edges configured to hold the computing device 102 to the goggles 202. The mounting clip 204 may comprise two components adjustably together via a tension member, such that the mounting clip 204 can receive computing devices 102 of varying size. Other arrangements are possible as well. As shown in FIG. 2, the mounting clip 204 may include a cutout 206. The cutout 206 may be configured to enable the camera 108 of the computing device 102 to be positioned in line with an eye of a subject. The mounting system 112 may further include one or more illumination features directed at the eye of the subject. Such illumination features may be one or more LED lights, or other lighting components that enable the camera 108 to better capture the eye of the subject. Further, such illumination features may be positioned on the googles 202, or on the mounting clip 204, among other locations.

In one particular embodiment, a first lens of the goggles 202 may include the mounting clip 204, and a second lens of the googles 202 may include an opaque lens. Such an arrangement may be advantageous to eliminate light artifacts and create a distraction free zone for the other eye for the methods described below. In another example arrangement, the mounting system goggles 202 may include a dark cuff-like cover to block any light shedding on the eyes from the ambient environment. Such a cover may help provide a dark environment for the camera to better track the eye of the subject. In another embodiment, the googles 202 may include a battery operated fan that circulates fresh air and reduces fogging inside of the goggles 202. In yet another embodiment, the mounting system 112 may include a mounting clip that can be removeably coupled to an existing helmet of the subject (e.g., a football helmet or a soldier's helmet). Other example mounting systems are possible as well.

Sensors 114 may include one or more of a proximity sensor, a vibration inducer, a microphone, an accelerometer, a gyroscope, and a magnetometer. The sensors 114 may be removeably positioned on the subject as discussed below. Further, the computing device 102 may be configured to communicate with the one or more sensors 114 using a communication link 116. As shown in FIG. 1, the communication link 116 is illustrated as a wireless connection; however, wired connections may also be used. For example, the communication link 116 may be a wired link via a serial bus such as a universal serial bus or a parallel bus. A wired connection may be a proprietary connection as well. The communication link 116 may also be a wireless connection via the communication interface 104 using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities.

Figure 3:
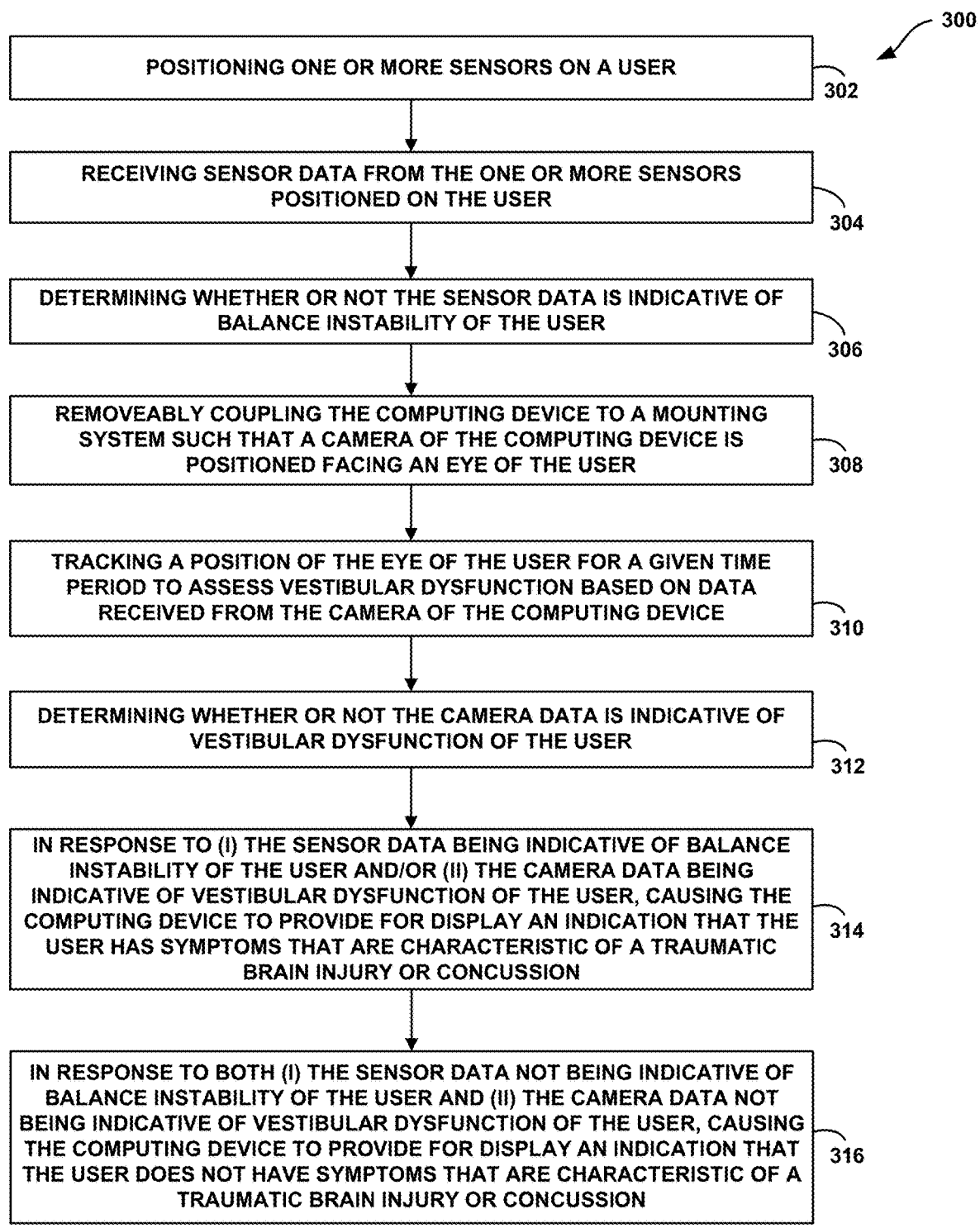
FIG. 3 is a flowchart illustrating an example method, according to an example embodiment.

FIG. 3 is a block diagram of an example method for detecting symptoms that are characteristic of a traumatic brain injury or concussion. Method 300 shown in FIG. 3 presents an embodiment of a method that could be used by the device 100 of FIG. 1, as an example. Method 300 may include one or more operations, functions, or actions as illustrated by one or more of blocks 302-314. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 300 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Figure 4:
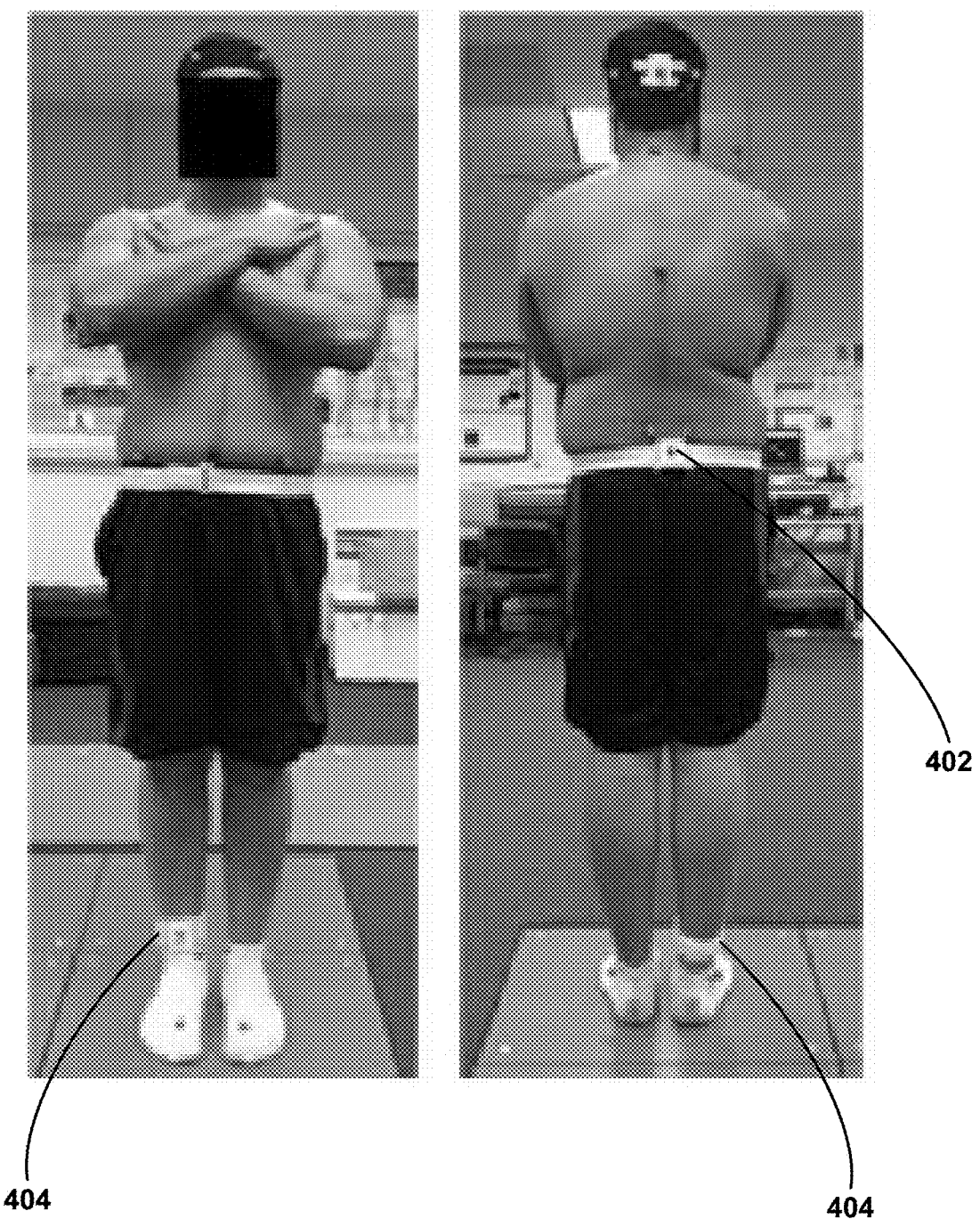
FIG. 4 illustrates an example sensor placement, according to an example embodiment.

Initially, at block 302, the method 300 includes positioning one or more sensors on a subject. The one or more sensors may be similarly configured to the sensors 114 described above in relation to FIG. 1. In one example, as shown in FIG. 4, positioning the one or more sensors on the subject comprises positioning a first sensor 402 of the one or more sensors on a hip of the subject, and positioning a second sensor 404 of the one or more sensors on an ankle of the subject.

Figure 5:
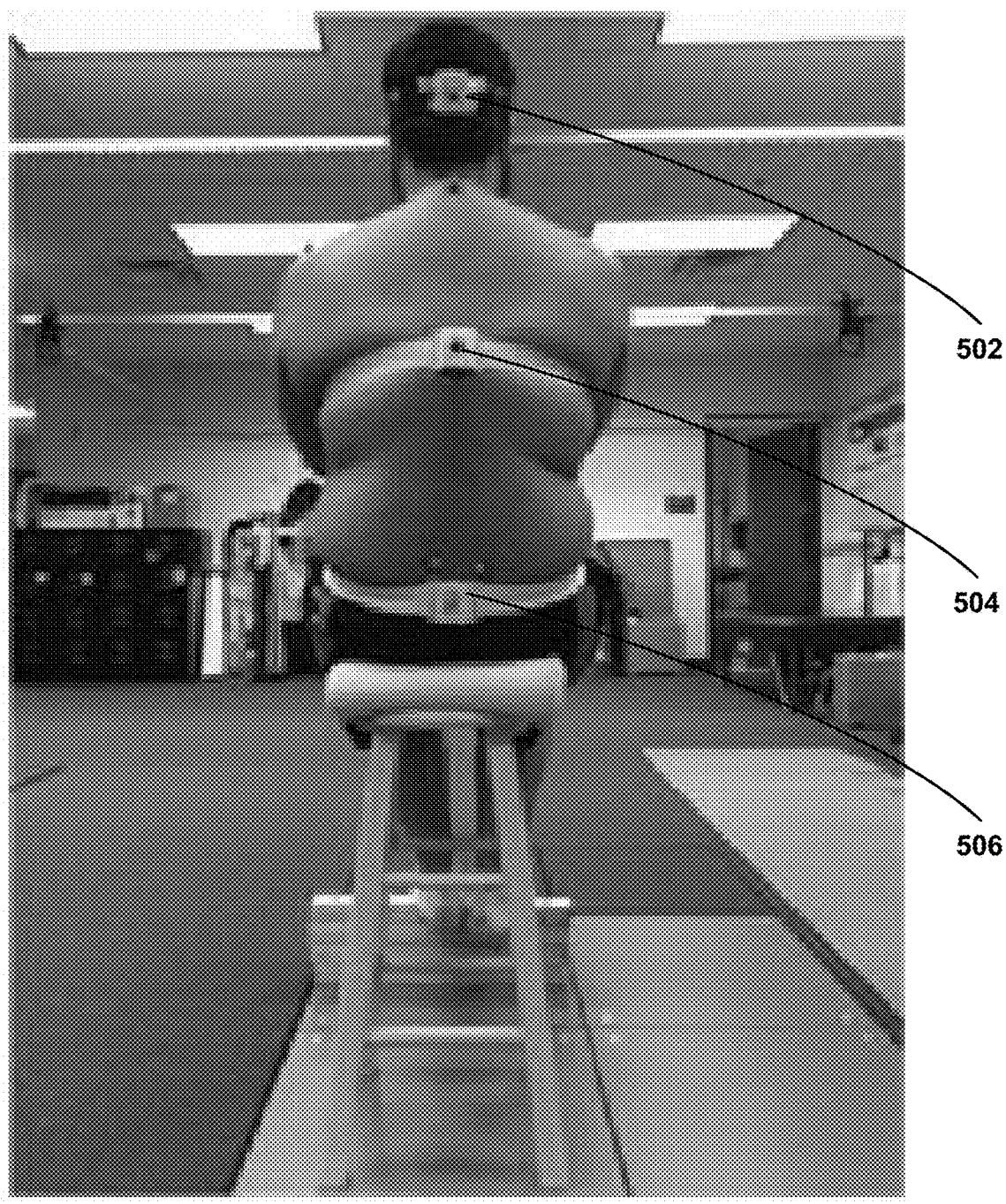
FIG. 5 illustrates another example sensor placement, according to an example embodiment.

In another example, as shown in FIG. 5, positioning the one or more sensors on the subject comprises positioning a first sensor 502 of the one or more sensors on a head of the subject, positioning a second sensor 504 of the one or more sensors on an ankle of the subject, and positioning a third sensor 506 of the one or more sensors on a hip of the subject. In such an example, the first sensor 502 may be implemented as part of or takes the form of a computing device, such as computing device 102 as described in FIG. 1. In another embodiment, the first sensor 502 may be implemented as part of or takes the form of a head-mountable device, such as mounting system 112 as described in FIG. 1. Other example embodiments are possible as well.

At block 304, the method 300 includes receiving sensor data from the one or more sensors positioned on the subject. As described above in relation to FIG. 1, the one or more sensors may transmit the sensor data to the computing device via a wired or wireless connection. In one example, the method 300 may further include the step of providing for display one or more visual or textual instructions for the subject and/or the individual administering the test. In such an example, the computing device receives the sensor data from the one or more sensors based on one or more actions performed by the subject corresponding to the one or more visual or textual instructions. In one example, the one or more visual or textual instructions comprise instructing the subject to stand in a stationary position for a given time period. In another example, the one or more visual or textual instructions comprise instructing the subject to sit in a stationary position for the given time period. The given time period may be between 15 and 60 seconds, for example. During the given time period, the one or more sensors may detect the movement of the subject. In the sitting position, the subject may be further instructed to positioned their legs at a 90 degree angle. Other instructions are possible as well.

Figure 6:
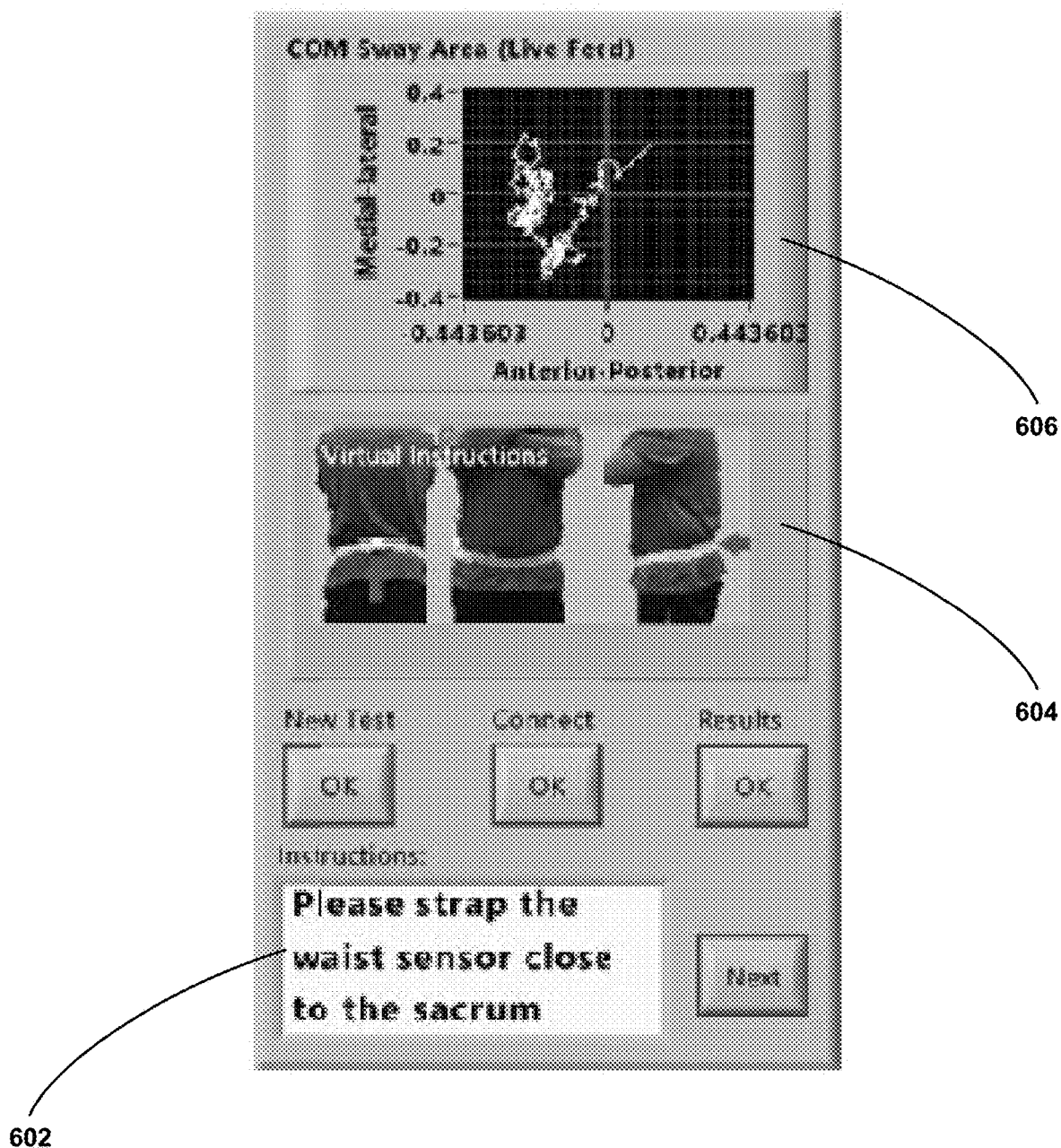
FIG. 6 illustrates applications of a user interface of an example computing device, according to an example embodiment.

FIG. 6 illustrates applications of a user interface of an example computing device, according to example embodiments. As shown in FIG. 6, the user interface may include textual instructions 602 as well as visual instructions 604. Further, the user interface may provide audio instructions as well. In addition, the user interface may display a graph 606 illustrating the received sensor data from the one or more sensors positioned on the subject.

At block 306, the method 300 includes determining whether the sensor data is indicative of balance instability of the subject. In one example, the computing device may include a "balance instability profile" stored in its data storage. The balance instability profile may include sensor data indicative of a typical subject having balance instability. More particularly, an example balance instability profile may include positional data from the one or more sensors corresponding to a typical subject having balance instability. The positional data may include a sway area (e.g., a total area covered by a given sensor of the one or more sensors), a sway velocity (e.g., an average velocity of a given sensor of the one or more sensors), a maximum displacement (e.g., a maximum displacement of a given sensor of the one or more sensors in both coronal and sagittal planes), and a head rotation. Thus, the computing device may compare the received sensor data to the balance instability profile to determine whether the sensor data is indicative of balance instability of the subject.

In a further example, the computing device may compare each measured positional data to a threshold value to determine whether the sensor data is indicative of balance instability of the subject. Such positional data may be provided on a per sensor basis, or may be provided as a combination of data received from each of the one or more sensors. As such, the computing device may compare a received sway area to a threshold sway area, a received sway velocity to a threshold sway velocity, a received maximum displacement to a threshold maximum displacement, and a received head rotation to a threshold head rotation. In one example, if one or more of the above comparisons results in a determination that the received positional data exceeds the threshold value, the computing device may determine that the sensor data is indicative of balance instability of the subject. In another example, the computing device may determine that the sensor data is indicative of balance instability of the subject only if two or more of the above comparisons result in a determination that the received positional data exceeds the threshold value. Other examples are possible as well.

At block 308, the method 300 includes removeably coupling the computing device to a mounting system such that a camera of the computing device is positioned facing an eye of the subject. In one example, the mounting system may be implemented as part of or takes the form of a head-mountable device, as described above in relation to FIG. 2.

At block 310, the method 300 includes tracking a position of the eye of the subject for a given time period to assess vestibular dysfunction based on data received from the camera of the computing device. In particular, the camera may be configured to record a video of the eye of the subject, and for each frame of the video, a high contrast image of the eye may be generated and the pupil location may be approximated to thereby track the position of the eye.

In one particular example, tracking the position of the eye of the subject for the given time period to assess vestibular dysfunction comprises (a) detecting, by the computing device, (i) an edge of an iris of the eye or (ii) a pupil centroid of the eye based on the data received from the camera of the computing device, and (b) determining, by the computing device, a displacement of (i) the edge of an iris of the eye or (ii) the pupil centroid of the eye for the given time period.

Figure 7:
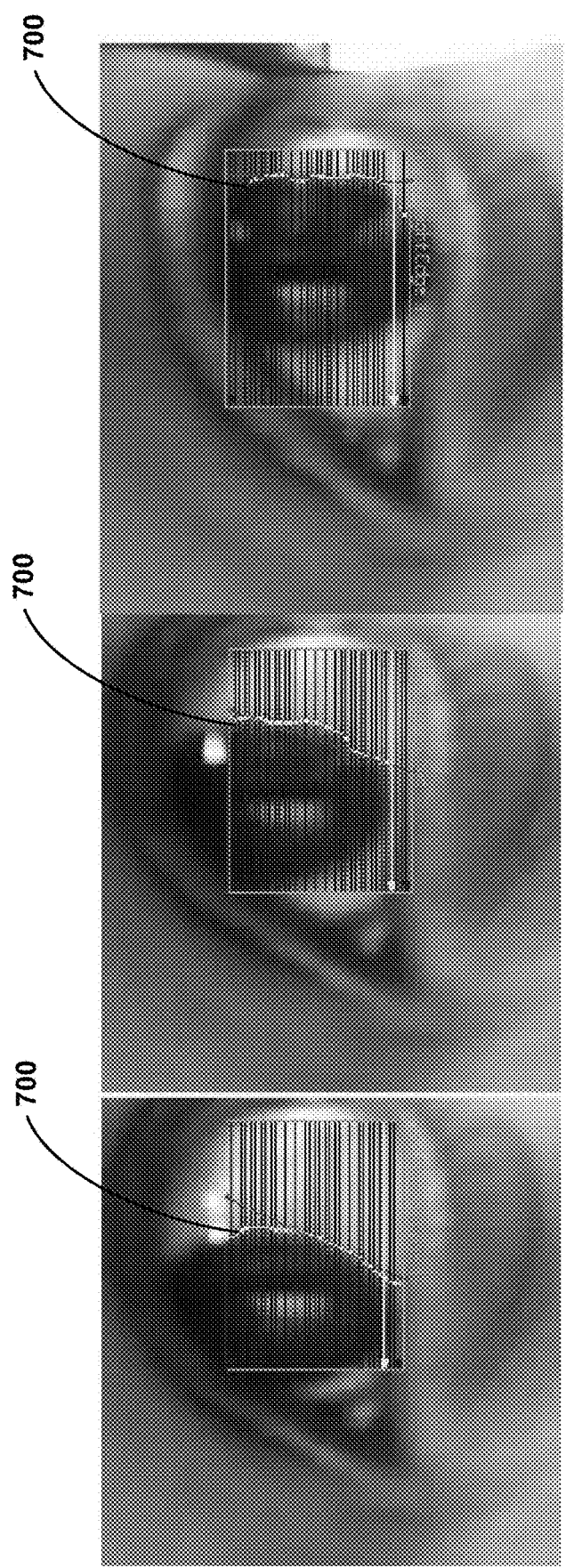
FIG. 7 illustrates an example edge detection of an iris of the eye of a subject, according to an example embodiment.

FIG. 7 illustrates an example edge detection of an iris of the eye of a subject, according to an example embodiment. As shown in FIG. 7, an edge 700 of the iris is detected based on a detected dark edge polarity. The relative position of the edge 700 of the iris may then be recorded to thereby track the position of the eye over the given time period. In another example, the pupil centroid of the eye may be tracked instead of the edge of the iris.

In one example, the method 300 may further include the step of providing for display one or more visual or textual instructions for the subject to track the position of the eye. In such an example, the computing device receives the camera data from the camera of the computing device based on one or more actions performed by the subject corresponding to the one or more visual or textual instructions.

Figure 8:
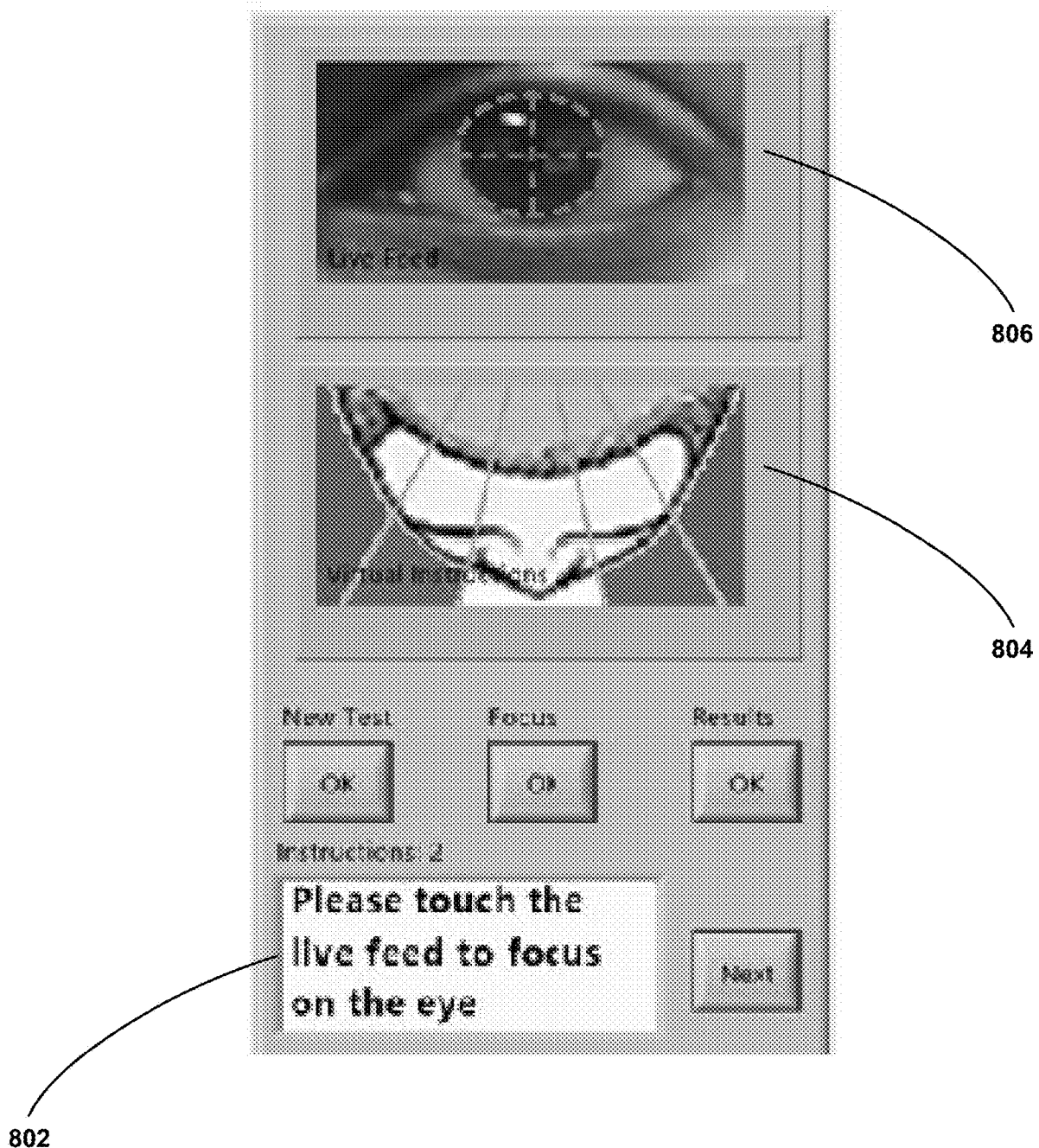
FIG. 8 illustrates applications of a user interface of an example computing device, according to example embodiments.

FIG. 8 illustrates applications of a user interface of an example computing device, according to example embodiments. As shown in FIG. 8, the user interface may include textual instructions 802 as well as visual instructions 804. Further, the user interface may provide audio instructions as well. In addition, the user interface may display a live feed 806 of the eye movement video so that the testing provider can see the eye being tracked.

In one example, the one or more visual or textual instructions include instructions to perform on or more vestibular function tests while tracking the eye of the subject. One such test is the head shaking test (HST). In HST, the individual administering the test is instructed to apply a 30° head anteflexion to the subject. Then at this head orientation, the subject is instructed to close his/her eyes and the individual administering the test will be instructed to quickly shakes the head of the subject within an approximate 30 degree range for 20 cycles in a ten second time period and then stop at a neutral position. The individual administering the test will then be instructed to tell the subject to open his/her eyes, and the eye tracking will begin. In this process, the sensor on the subject's head or the sensor in the computing device 102 will provide the number of shaking cycles completed and the angular measurement of the head anteflexion as well as the left and right head shaking.

Another such test is the head impulse test (HIT). In HIT, the subject is instructed to focus on the nose of the individual administering the test. The subject's head is then quickly rotated using a thrust motion to the left by about 20 degrees and then stopped. At this point, the eye tracking would be activated to track the movements of the eye of the subject for about 10 seconds. Similarly, the head is thrust to the right by about 20 degrees and then stopped, and the eye tracking is activated. In this process, the sensor on the subject's head or the sensor in the computing device 102 will provide the angular measurement of the head thrust.

Another such test is the gaze-evoked nystagmus test (GENT). In GENT, the eye tracking is activated and the subject is instructed to stare straight ahead at the nose of the individual administering the test for about ten seconds. The test will then be repeated when the individual administering the test uses their finger to direct the subject to stare to the right and to the left while the eye of the subject is being tracked. In this process, the computing device 102 will provide the measure of the ten seconds.

Yet another such test is the vibration-induced nystagmus test (VINT). In VINT, the person performing the test places a vibration sensor capable of delivering approximately 90-100 Hz to the mastoid bone of the subject for about 10 seconds while the eye movement of the subject is tracked. The test may be repeated by applying vibration to both left and right mastoid bone. In one example, the vibration sensor may be coupled to or be implemented as part of the mounting system.

At block 312, the method 300 includes determining whether the camera data is indicative of vestibular dysfunction of the subject. In one example, the computing device may include a "vestibular dysfunction profile" stored in its data storage. The vestibular dysfunction profile may include eye tracking data indicative of a typical subject having vestibular dysfunction, such as nystagmus. More particularly, an example vestibular dysfunction profile may include a saw-tooth like waveform in the eye position data. Thus, if the received camera data is threshold similar to the vestibular dysfunction profile, the computing device may determine that the camera data is indicative of vestibular dysfunction of the subject.

At block 314, the method 300 includes in response to (i) the sensor data being indicative of balance instability of the subject and/or (ii) the camera data being indicative of vestibular dysfunction of the subject, causing the computing device to provide for display an indication that the subject has symptoms that are characteristic of a traumatic brain injury or concussion. Such an indication may be a textual indication, a visual indication, and/or audio indication. Further, such an indication may be color coded. For example, the indication that the subject has symptoms that are characteristic of a traumatic brain injury or concussion may be provided in red lettering or a red background. Other examples are possible as well.

At block 316, the method 300 includes both (i) the sensor data not being indicative of balance instability of the subject and (ii) the camera data not being indicative of vestibular dysfunction of the subject, cause the computing device to provide for display an indication that the subject does not have symptoms that are characteristic of a traumatic brain injury or concussion. Such an indication may be a textual indication, a visual indication, and/or audio indication. Further, such an indication may be color coded. For example, the indication that the subject does not have symptoms that are characteristic of a traumatic brain injury or concussion may be provided in green lettering or a green background. Other examples are possible as well.

Figure 9:
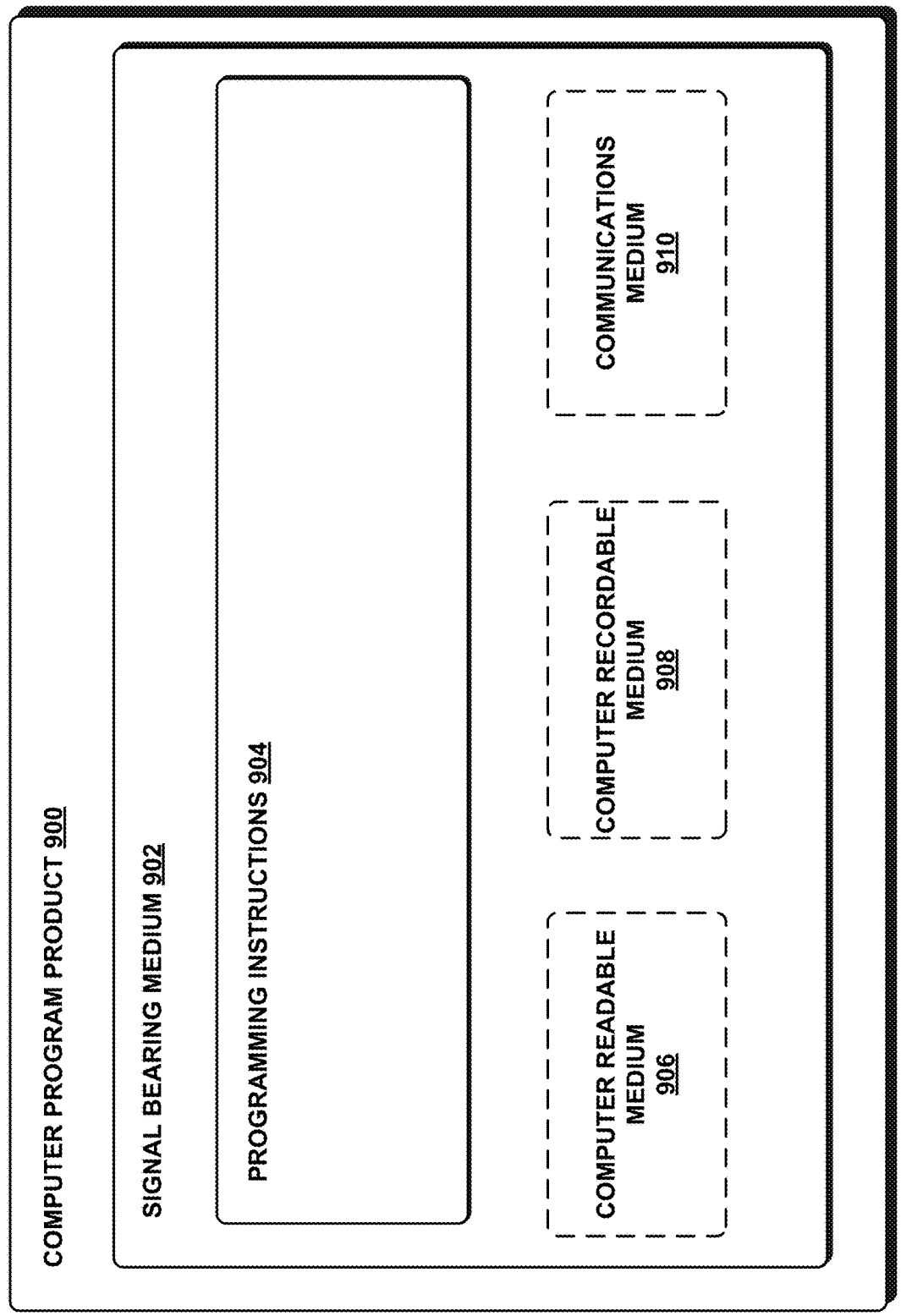
FIG. 9 illustrates a computer-readable medium configured according to an example embodiment.

FIG. 9 illustrates a computer-readable medium configured according to an example implementation. In example implementations, the example system can include one or more processors, one or more forms of memory, one or more input devices/interfaces, one or more output devices/interfaces, and machine-readable instructions that when executed by the one or more processors cause the system to carry out the various operations, tasks, capabilities, etc., described above.

As noted above, in some implementations, the disclosed system can perform actions that may be implemented by computer program instructions encoded on a non-transitory computer-readable storage media in a machine-readable format, or on other non-transitory media or articles of manufacture. FIG. 9 is a schematic illustrating a conceptual partial view of an example computer program product that includes a computer program for executing a computer process on a computing device, arranged according to at least some implementations presented herein.

In one implementation, the example computer program product 900 is provided using a signal bearing medium 902. The signal bearing medium 902 may include one or more programming instructions 904 that, when executed by one or more processors may provide functionality or portions of the functionality described above with respect to FIGS. 1-8. In some examples, the signal bearing medium 902 can be a computer-readable medium 906, such as, but not limited to, a hard disk drive, a Compact Disc (CD), a Digital Video Disk (DVD), a digital tape, memory, etc. In some implementations, the signal bearing medium 902 can be a computer recordable medium 908, such as, but not limited to, memory, read/write (R/W) CDs, R/W DVDs, etc. In some implementations, the signal bearing medium 902 can be a communications medium 910, such as, but not limited to, a digital and/or an analog communication medium (e.g., a fiber optic cable, a waveguide, a wired communications link, a wireless communication link, etc.). Thus, for example, the signal bearing medium 902 can be conveyed by a wireless form of the communications medium 910.

The one or more programming instructions 904 can be, for example, computer executable and/or logic implemented instructions. In some examples, a computing device such as the processor 118 of FIG. 1 is configured to provide various operations, functions, or actions in response to the programming instructions 904 conveyed to the processor 118 by one or more of the computer-readable medium 906, the computer recordable medium 908, and/or the communications medium 910.

The non-transitory computer-readable medium 908 could also be distributed among multiple data storage elements, which could be remotely located from each other. The device that executes some or all of the stored instructions could be a client-side computing device. Alternatively, the device that executes some or all of the stored instructions could be a server-side computing device.

Within some examples herein, operations may be embodied on a computer program product (e.g., a tangible computer readable storage medium or non-transitory computer readable medium) that includes instructions executable to perform the operations.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

What is claimed is:

1. A system comprising:
   one or more sensors;
   a mounting system configured to removeably mount a computing device thereto, wherein the mounting system includes a mounting clip having a first edge and a second edge configured to removeably retain the computing device therebetween, wherein the mounting clip includes a cutout configured to be aligned with a camera of the computing device such that a field of view of the camera of the computing device is positioned facing a first eye of a subject when the computing device is removeably mounted to the mounting system, and wherein a second eye of the subject is covered by an opaque material such that the field of view of the camera is not positioned facing the second eye of the subject when the computing device is removeably mounted to the mounting system;
   a control system, wherein the control system is configured to:
     receive sensor data from the one or more sensors, wherein the one or more sensors are configured to be removeably positioned on a subject, and wherein at least one of the one or more sensors is positioned on a body part of the subject other than a head of the subject;
     determine whether or not the sensor data is indicative of balance instability of the subject;
     track a position of the first eye of the subject for a given time period to assess vestibular dysfunction based on data received from the camera of the computing device;
     determine whether or not the camera data is indicative of vestibular dysfunction of the subject;
     in response to (i) the sensor data being indicative of balance instability of the subject and/or (ii) the camera data being indicative of vestibular dysfunction of the subject, cause the computing device to provide for display an indication that the subject has symptoms that are characteristic of a traumatic brain injury or concussion; and
     in response to both (i) the sensor data not being indicative of balance instability of the subject and (ii) the camera data not being indicative of vestibular dysfunction of the subject, cause the computing device to provide for display an indication that the subject does not have symptoms that are characteristic of a traumatic brain injury or concussion.

2. The system of claim 1, wherein the mounting system is implemented as part of or takes the form of a head-mountable device.

3. The system of claim 2, wherein the head-mountable device includes goggles, wherein a first lens of the goggles includes the mounting system, and wherein a second lens of the goggles includes an opaque lens.

4. The system of claim 1, wherein tracking the position of the first eye of the subject for the given time period to assess vestibular dysfunction comprises:
   detect (i) an edge of an iris of the first eye or (ii) a pupil centroid of the first eye based on the data received from the camera of the computing device; and
   determine a displacement of (i) the edge of an iris of the first eye or (ii) the pupil centroid of the first eye for the given time period.

5. The system of claim 1, wherein the one or more sensors comprise one or more of a proximity sensor, a vibration inducer, a microphone, an accelerometer, a gyroscope, and a magnetometer.

6. The system of claim 1, wherein the one or more sensors comprises two sensors, wherein a first sensor is configured to be removeably positioned on a hip of the subject, and wherein a second sensor is configured to be removeably positioned on an ankle of the subject.

7. The system of claim 1, wherein the one or more sensors comprises three sensors, wherein a first sensor is configured to be removeably positioned on the head of the subject, wherein a second sensor is configured to be removeably positioned on a back of the subject, and wherein a third sensor is configured to be removeably positioned on a hip of the subject.

8. The system of claim 1, wherein the control system is further configured to:
   provide for display one or more visual or textual instructions for the subject, wherein the control system receives the sensor data from the one or more sensors based on one or more actions performed by the subject corresponding to the one or more visual or textual instructions.

9. The system of claim 1, wherein the mounting system includes one or more illumination features directed at the first eye of the subject.

10. A method comprising:
    positioning one or more sensors on a subject, wherein at least one of the one or more sensors is positioned on a body part of the subject other than a head of the subject;
    receiving, at a computing device, sensor data from the one or more sensors positioned on the subject;
    determining, by the computing device, whether the sensor data is indicative of balance instability of the subject;
    removeably coupling the computing device to a mounting system, wherein the mounting system includes a mounting clip having a first edge and a second edge configured to removeably retain the computing device therebetween, wherein the mounting clip includes a cutout configured to be aligned with a camera of the computing device such that a field of view of the camera of the computing device is positioned facing a first eye of the subject when the computing device is removeably coupled to the mounting system, and wherein a second eye of the subject is covered by an opaque material such that the field of view of the camera is not positioned facing the second eye of the subject when the computing device is removeably mounted to the mounting system;

tracking, by the computing device, a position of the first eye of the subject for a given time period to assess vestibular dysfunction based on data received from the camera of the computing device;

determining, by the computing device, whether the camera data is indicative of vestibular dysfunction of the subject;

in response to (i) the sensor data being indicative of balance instability of the subject and/or (ii) the camera data being indicative of vestibular dysfunction of the subject, causing the computing device to provide for display an indication of symptoms that are characteristic of a traumatic brain injury or concussion; and in response to both (i) the sensor data not being indicative of balance instability of the subject and (ii) the camera data not being indicative of vestibular dysfunction of the subject, causing the computing device to provide for display an indication that the subject does not have symptoms that are characteristic of a traumatic brain injury or concussion.

11. The method of claim 10, wherein positioning the one or more sensors on a subject comprises:

positioning a first sensor of the one or more sensors on a hip of the subject; and positioning a second sensor of the one or more sensors on an ankle of the subject.

12. The method of claim 10, wherein positioning the one or more sensors on a subject comprises:

positioning a first sensor of the one or more sensors on a head of the subject;

positioning a second sensor of the one or more sensors on an ankle of the subject; and positioning a third sensor of the one or more sensors on a hip of the subject.

13. The method of claim 10, wherein tracking the position of the first eye of the subject for the given time period to assess vestibular dysfunction comprises:

detecting, by the computing device, (i) an edge of an iris of the first eye or (ii) a pupil centroid of the first eye based on the data received from the camera of the computing device; and determining, by the computing device, a displacement of (i) the edge of an iris of the first eye or (ii) the pupil centroid of the first eye for the given time period.

14. The method of claim 10, further comprising:

providing for display one or more visual or textual instructions for the subject, wherein the computing device receives the sensor data from the one or more sensors based on one or more actions performed by the subject corresponding to the one or more visual or textual instructions.

15. The method of claim 14, wherein the one or more visual or textual instructions comprise instructing the subject to stand in a stationary position.

16. The method of claim 14, wherein the one or more visual or textual instructions comprise instructing the subject to sit in a stationary position.

17. A non-transitory computer-readable medium storing instructions that, when executed by one or more processors of a computing device, cause the computing device to perform functions comprising:

receiving sensor data from one or more sensors positioned on a subject, wherein at least one of the one or more sensors is positioned on a body part of the subject other than a head of the subject;

determining whether the sensor data is indicative of balance instability of the subject;

tracking a position of a first eye of the subject for a given time period to assess vestibular dysfunction based on data received from a camera of the computing device, wherein the computing device is removeably coupled to a mounting system, wherein the mounting system includes a mounting clip having a first edge and a second edge configured to removeably retain the computing device therebetween, wherein the mounting clip includes a cutout configured to be aligned with the camera of the computing device such that a field of view of the camera of the computing device is positioned facing the first eye of the subject when the computing device is removeably coupled to the mounting system, and wherein a second eye of the subject is covered by an opaque material such that the field of view of the camera is not positioned facing the second eye of the subject when the computing device is removeably mounted to the mounting system;

determining whether the camera data is indicative of vestibular dysfunction of the subject;

in response to (i) the sensor data being indicative of balance instability of the subject and/or (ii) the camera data being indicative of vestibular dysfunction of the subject, causing the computing device to provide for display an indication that the subject has symptoms that are characteristic of a traumatic brain injury or concussion; and in response to both (i) the sensor data not being indicative of balance instability of the subject and (ii) the camera data not being indicative of vestibular dysfunction of the subject, causing the computing device to provide for display an indication that the subject does not have symptoms that are characteristic of a traumatic brain injury or concussion.

18. The non-transitory computer-readable medium of claim 17, wherein tracking the position of the first eye of the subject for the given time period to assess vestibular dysfunction comprises:

detecting (i) an edge of an iris of the first eye or (ii) a pupil centroid of the first eye based on the data received from the camera of the computing device; and determining a displacement of (i) the edge of an iris of the first eye or (ii) the pupil centroid of the first eye for the given time period.

* * * * *